(12) United States Patent
Delaney

(10) Patent No.: US 7,901,650 B2
(45) Date of Patent: Mar. 8, 2011

(54) POROUS BETA-TRICALCIUM PHOSPHATE AND METHODS FOR PRODUCING THE SAME

(75) Inventor: David Delaney, Scotts Valley, CA (US)

(73) Assignee: Skeletal Kinectics, LLC, Cupertino, CA (US)

( * ) Notice: Subject to any disclaimer, the term of this patent is extended or adjusted under 35 U.S.C. 154(b) by 993 days.

(21) Appl. No.: 11/165,564

(22) Filed: Jun. 22, 2005

(65) Prior Publication Data

US 2006/0292200 A1 Dec. 28, 2006

(51) Int. Cl.
*C01B 25/26* (2006.01)
*A61K 31/78* (2006.01)

(52) U.S. Cl. .......................... 423/308; 424/423

(58) Field of Classification Search .................. 501/80, 501/123; 623/23.63; 424/603, 601, 602, 424/600, 604, 606, 607, 623; 423/308
See application file for complete search history.

(56) References Cited

U.S. PATENT DOCUMENTS

| | | | |
|---|---|---|---|
| 4,717,556 A | 1/1988 | Kawamura et al. | |
| 5,171,720 A | 12/1992 | Kawakami | |
| 5,491,082 A | 2/1996 | Suzuki et al. | |
| 5,939,039 A | 8/1999 | Sapieszko et al. | |
| 6,713,420 B2 * | 3/2004 | Imura et al. ................. | 501/80 |
| 7,223,356 B2 * | 5/2007 | Chartier et al. ............. | 252/500 |
| 2002/0114755 A1 | 8/2002 | Jordanova-Spassova | |
| 2003/0036800 A1 * | 2/2003 | Meredith ................... | 623/23.63 |
| 2003/0049328 A1 | 3/2003 | Dalal et al. | |
| 2003/0180376 A1 * | 9/2003 | Dalal et al. ................ | 424/602 |
| 2003/0235622 A1 | 12/2003 | Tas | |
| 2004/0019385 A1 | 1/2004 | Ayers et al. | |
| 2004/0076685 A1 * | 4/2004 | Tas ............................. | 424/602 |
| 2004/0099998 A1 * | 5/2004 | Ishikawa et al. ........... | 264/603 |

FOREIGN PATENT DOCUMENTS

JP 11232338 3/2001

OTHER PUBLICATIONS

Habibovic et al. "3D Microenvironment as Essential Element for Osteoinduction by Biomaterials," Biomaterials (2005) 26:3565-3575.
Dong et al. "Promotion of Bone Formation Using Highly Pure Porous β-TCP Combined with Bone Marrow-Derived Osteoprogenitor Cells," Blomaterials (2002) 23:4493-4502.
Shihong et al. "Macroporous Biphasic Calcium Phosphate Scaffold with High Permeability/Porosity Ratio," Tissue Engineering (2003) 9: 535-548.
Bohner et al. "Synthesis and Characterization of Porous β-Tricalcium Phosphate Blocks," Biomaterials (2005) 26:6099-6105.
Oliveira et al. "Effect of Process Parameters on the Characteristics of Porous Calcium Phosphate Ceramics for Bone Tissue Scaffolds," Artificial Organs (2003) 27(5):406-411.

* cited by examiner

*Primary Examiner* — Karlheinz R Skowronek
*Assistant Examiner* — Ali Soroush
(74) *Attorney, Agent, or Firm* — Bozicevic, Field & Francis LLP; Bret E. Field

(57) ABSTRACT

Methods are provided for producing porous β-Tricalcium Phosphate (β-TCP). In the subject methods, β-TCP is combined with graphite to produce an intermediate greenware product. The intermediate greenware product is then sintered to produce porous β-TCP. The subject methods and compositions produced thereby find use in a variety of applications.

9 Claims, 1 Drawing Sheet

POROUS BETA-TRICALCIUM PHOSPHATE AND METHODS FOR PRODUCING THE SAME

BACKGROUND

The need for biomaterials in orthopedic and dental applications has increased as the world population ages. A significant amount of research into biomaterials for orthopedic and dental uses has attempted to address the functional criteria for orthopedic and dental reconstruction within the human body. The materials that have become available for such uses have improved in recent years. All such materials must be biocompatible, however, and the degree of biocompatibility exhibited by materials that are candidates for such use is always a major concern. Biomaterials useful for orthopedic and dental reconstructions must have high strength, must be able to be immediately affixed to the situs for reconstruction, must bond strongly to bone, and must give rise to strong, highly resilient restorations.

Tricalcium phosphate (TCP) materials are considered as one of the most preferred material types in the filed of orthopedic, restorative and reconstructive surgery, and are particularly useful for bone replacement, spinal repair, reconstructive, cosmetic and other surgeries. Tricalcium phosphate occurs in at least two forms. The first is the monoclinic form, called α-tricalcium phosphate. The second form is the orthorhombic form, called β-tricalcium phosphate. β-tricalcium phosphate (β-TCP) is the preferred form for bone replacements in many applications because it is capable of being resorbed by the body, facilitating bone remodeling. At appropriate porosities, β-TCP resembles natural bone and provides a scaffold for in-migration of osteogenic cells, resulting in production of bone directly attached to the β-TCP implant. The body will generally resorb β-TCP within about two years, replacing it with natural bone.

A variety of different protocols have been developed for producing β-TCP compositions for use in the medical and other fields. However, while a large number of different protocols have been developed, there is a continued need for the development of yet more advanced methods of producing β-TCP compositions.

RELEVANT LITERATURE

U.S. patents and published U.S. patent applications of interest include U.S. Pat. Nos. 5,491,082; 5,171,720; 4,717,556; 20040019385; 20030235622; 20030180376; 20030049328; 20020114755; the disclosures of which are herein incorporated by reference.

SUMMARY OF THE INVENTION

Methods are provided for producing porous β-Tricalcium Phosphate (β-TCP). In the subject methods, β-TCP is combined with graphite to produce an intermediate greenware product. The intermediate greenware product is then sintered to produce porous β-TCP. The subject methods and compositions produced thereby find use in a variety of applications.

DESCRIPTION OF THE SPECIFIC EMBODIMENTS

Figure 1:
FIG. 1 provides a photograph of material produced according to a representative embodiment of the invention.

Methods are provided for producing porous β-Tricalcium Phosphate (β-TCP). In the subject methods, β-TCP is combined with graphite to produce an intermediate greenware product. The intermediate greenware product is then sintered to produce porous β-TCP. The subject methods and compositions produced thereby find use in a variety of applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

In further describing the subject invention, the subject methods will be described first, followed by a description of the compositions produced thereby and representative applications in which the compositions find use.

Methods

As summarized above, the invention provides methods of producing porous β-TCP compositions, e.g., in the form of powders or granules. In practicing the subject methods, an initial tricalcium phosphate, e.g., β-tricalcium phosphate, is combined with graphite to produce a graphite containing tricalcium phosphate composition, e.g., to produce a "greenware" composition. The resultant greenware composition is then sintered to product the desired porous tricalcium phosphate product. Each of these steps is now described in greater detail below.

The initial source of tricalcium phosphate may be any convenient source, where the initial source may be prepared de novo or purchased from a commercial vendor. The initial tricalcium phosphate source will typically be β-TCP. β-TCP is available from a variety of commercial sources, but may also be prepared from readily available reactants. For example, β-TCP may be prepared by first combining stoichiometric amounts of $CaHPO_4$ and $CaCO_3$ to get a resultant product that has a calcium to phosphate ratio of 1.5:1. The stoichiometric amounts of $CaHPO_4$ and $CaCO_3$ are added to an aqueous reaction volume. The solids in the resultant slurry are then separated from the liquids under pressure, where the pressure may range from about 5-30 psi, more usually from about 5 to 25 psi and typically from about 8 to 15 psi to yield the final β-TCP. Commercial vendors of β-TCP include, but are not limited to: Fluka Chemika, Sigma Chemical and the like. In certain embodiments, the β-TCP will be a powder, where the powder may in certain embodiments have an average particle size of less than about 100 microns, such as less than about 50 microns, where in representative embodiments, the average particle size ranges from about 10 to about 20 microns.

As reviewed above, in the first step of the subject methods, the initial source of β-TCP is combined with graphite. The term graphite has its art accepted meaning and refers to a polymorph of carbon that is characterized as having a black silver color that has a metallic to dull luster and is flaky upon fracture. The graphite that is combined with initial source of β-TCP is, in certain embodiments, a particulate composition, having particles that range in size from small granules to large flakes, e.g., from about 5 to about 250 mesh, e.g., from about 10 to about 200 mesh. In certain embodiments, the graphite composition that is employed is one that includes two different populations of particle sizes, where one of the populations has a particle size that is larger than the other, e.g., by at least about 0.5 fold, such as by a least about 10 fold, where in certain embodiments, mesh size of the large particles ranges from about 5 to 20, such as from about 5 to 25, e.g., 10, while the mesh size of the smaller particles ranges from about 100 to about 500, such as from about 150 to 250, e.g., 200. Where the graphite includes populations of both large and small graphite particles, the weight ratio of large to small particles in the graphite source may range from about 0.5 to 1 to about 1 to 0.5, and in many representative embodiments is 1 to 1, or substantially the same as 1 to 1.

The amount of initial β-TCP and the amount of graphite that are combined in the first step of the subject methods may vary. In certain embodiments, the amount of the initial β-TCP source is greater than the amount of the graphite source, e.g., by at least about 2 fold, such as at least about 4 fold, including at least about 5 fold or more. In these embodiments, the mass ratio of the mass of first β-TCP to the mass of the graphite may range from about 10 to about 1, e.g., from about 8 to about 1, such as from about 5 to about 1.

In preparing the greenware according to this first step of the subject invention, the β-TCP and graphite components are typically combined with a fluid in an amount sufficient to produce a slurry or paste composition. The fluid can be any of a variety of setting fluids known to those of skill in the art. Fluids of interest include, but are not limited to: water (including purified forms thereof, aqueous alkanol solutions, e.g. glycerol, where the alkanol is present in minor amounts, etc. In many embodiments, the fluid is water.

The ratio of the β-TCP and graphite components dry reactants to fluid (i.e. the liquid to solids ratio) is selected to provide for a composition of suitable characteristics, where the composition should be easily mixable in order to facilitate production of a homogeneous combination or mixture of the β-TCP and graphite components. In representative embodiments, the liquids to solids ratio employed in the subject methods typically ranges from about 0.2 to 2.0, such as from about 0.5 to 1.5, each from about 0.75 to 1.25, including from about 0.0.90 to about 1.20.

Where desired, a binder may be combined with the β-TCP and graphite components. In representative embodiments, the binder is biodegradable, biocompatible and has fluid flow properties. The binders contemplated as useful herein include, but are not limited to: art-recognized suspending agents, viscosity-producing agents, gel-forming agents and emulsifying agents. Other candidates are agents used to suspend ingredients for topical, oral or parental administration. Yet other candidates are agents useful as tablet binders, disintegrants or emulsion stabilizers. Still other candidates are agents used in cosmetics, toiletries and food products. Reference manuals such as the USP XXII-NF XVII (The Nineteen Ninety U.S. Pharmacopeia and the National Formulary (1990)) categorize and describe such agents. Representative binders of interest include, but are not limited to: resorbable macromolecules from biological or synthetic sources including sodium alginate, hyaluronic acid, cellulose derivatives such as alkylcelluloses including methylcellulose, carboxy methylcellulose, carboxy methylcellulose sodium, carboxy methylcellulose calcium or other salts, hydroxy alkylcelluloses including hydroxypropyl methylcellulose, hydroxybutyl methylcellulose, hydroxyethyl methylcellulose, hydroxyethyl cellulose, alkylhydroxyalkyl celluloses including methylhydroxyethyl cellulose, collagen, peptides, polysaccharides, mucin, chrondroitin sulfate and the like.

In representative embodiments, the binder is selected from a class of polysaccharides, where representative members of the class include, but are not limited to: dextran, dextran sulfate, diethylaminoethyl dextran, dextran phosphate, starch, fractionated starch, amylopectin, agar, gum arabic, pullullan, agarose, carrageenan, dextrins, fructans, inulin, mannans, xylans, arabinans, glycogens, glucans, xanthan gum, guar gum, locust bean gum, tragacanth gum, karaya gum, and derivatives and mixtures thereof.

When present in the composition, the amount of binder present in the composition is, in representative embodiments, substantially less than total mass of all of the dry components used to produce the greenware composition, where the mass ratio of binder to total mass of dry ingredients ranges, in certain embodiments, from about 1 to 50, such as from about 1 to 30, including from about 1 to 25.

In making the greenware composition, the requisite amounts of dry reactants and fluid are combined under conditions sufficient to produce the product composition with the desired physical characteristics. As such, the dry and liquid components are typically combined under agitation or mixing conditions, such that a homogenous composition is produced from the dry and liquid components. Mixing may be accomplished using any convenient means, including manual mixing, e.g., with a mortar and pestle.

Following combination of the dry and fluid components to produce a homogeneous mixture of β-TCP and graphite, as reviewed above, any free water in the mixture is then removed to prepare the mixture of sintering, as reviewed in greater detail below. Free water in the mixture may be removed using any convenient protocol. In certain embodiments of interest, free water is removed by maintaining the composition at an elevated pressure and temperature for a time sufficient to remove free water from the composition. In these embodiments, the composition is maintained at a pressure of greater than about 1.0 atm, such as at least about 1.25 atm, including a pressure of at least about 1.5 atm, up to about 5 atm or greater, where in representative embodiments, the pressure may range from about 1.25 to about 2 atm. With respect to the temperature of these embodiments, the elevated temperature may be at least about 35° C., such as at least about 50° C., including at least about 100° C., and may be as high as about 150° C. or higher, e.g., as high as about 200° C. or higher, and in certain embodiments ranges from about 75 to about 175° C., such as from about 100 to about 150° C., including from about 100 to about 125° C. In these step, the composition is maintained at the elevated temperature and pressure for a period of time sufficient to remove the free-water from the composition to produce a greenware product of desired properties, where all the water has evaporated. In representative embodiments, the composition is maintained at the elevated pressure and temperature for a period of that is at least about 5 minutes, such as at least about 10 minutes, where the period of time may be as long as about 60 minutes or longer, but in representative embodiments ranges from about 5 to about 25 minutes, e.g., from about 10 to about 20 minutes, including about 15 minutes.

The above process results in production of a greenware product that is a homogeneous composition of β-TCP and graphite, where the composition is substantially, if not completely, free of uncombined water. By substantially free is meant that the amount of uncombined water remaining in the composition is less than about 20%, such as less than about 10% including less than about 1% by weight.

In the next step of the subject methods, the resultant greenware product composition is sintered at a temperature sufficient to produce the desired final porous β-TCP product. By sintering is meant that the greenware product is maintained at a sintering temperature for a period of time sufficient to convert the graphite in the greenware to $CO_2$ and thereby separate the graphite from the β-TCP in the greenware to produce the desired porous β-TCP product. The sintering temperature employed in this step of the subject methods may vary, and in representative embodiments ranges from about 1000 to about 1500° C., such as from about 1100 to about 1300° C., including 1150 to about 1250° C., such as 1190 to about 1220° C., e.g., 1200° C. The greenware is maintained at the sintering temperature for a time sufficient to convert the substantially all, if not all, of the graphite from the greenware, where in representative embodiments the greenware is maintained at the temperature for a period of time ranging from about 5 to about 15 hours, including from about 6 to about 12 hours, such as from about 7 to about 10 hours, e.g., 8 hours. By substantially all of the graphite being converted to $CO_2$ is meant that the amount of graphite, if any, remaining in the composition following sintering is not more than about 10%, such as not more than about 5%, including not more than about 1% by weight of the original amount of graphite that was in the greenware prior to sintering. In certain embodiments, sintering occurs entirely in an oxidizing atmosphere, e.g., air. In yet other embodiments, the sintering process is started in a neutral atmosphere, e.g., argon, nitrogen, etc., and then completed in an oxidizing atmosphere, e.g., air. For example, in embodiments where it is desired to ensure that graphite does not convert to $CO_2$ until just before the tricalcium phosphate liquid phase is reached, e.g., around 1200°, the sintering process may be started in a neutral atmosphere, where the neutral atmosphere is then changed to an oxidizing atmosphere following a period of time sufficient for the greenware to reach the desired temperature, e.g., around 1200°.

Sintering can be achieved with furnaces such as cupola furnaces, crucible furnaces, open-hearth furnaces, induction furnaces, electric-arc furnaces, or the like, as is known in the art.

The above sintering step produces a solid porous β-TCP product. The resultant product is characterized by being substantially Where desired, the resultant porous β-TCP product can be milled into a particulate composition for subsequent use. In certain embodiments, the size of the particles may range from about 10 to about 1000 µm, such as from about 100 to about 500 µm. In representative embodiments, the milled composition will have a mean particle size ranging from about 200 to about 300 µm, such as from about 225 to about 275 µm. Although dependent on the type of milling employed, milling times may range from 0.1 to 80 hr, usually 0.5 to 4 hr. Any convenient means of milling may be employed, including ball milling, jet milling, SWECO® milling, attritor milling, hammer milling, planetary ball milling, and the like.

Porous β-TCP

The above-described method provides a porous β-TCP having a pore size and granule size of desired properties, e.g., as appropriate for bone formation, bone regeneration, and bone repair at a defect site in a human or animal. The porous β-TCP body described in this invention comprises β-TCP having a multiplicity of pores. The pore diameter size of the porous β-TCP of this invention is in the range of about 1 to about 100 µm. In one embodiment, the pores are spherical and uniformly distributed. In representative embodiments, the β-TCP comprises β-TCP that is 95-100% pure.

The porous β-TCP material of the present invention may have any shape and size. In one embodiment, the porous β-TCP is granular and has a particle size between about about 0.1 and about 3 mm. In representative embodiments, the total porosity of the β-TCP product, e.g., as measured using the mercury intrusion parameter method or equivalent methods, ranges from about 5 to about 80%, such as from about 40 to about 80%, including from about 65 to about 75%, e.g., about 70%.

Utility

The subject porous β-TCP product can be used in a variety of different applications. In a first representative application, the subject β-TCP product is used in an implant device, e.g., for promoting bone formation, regeneration and repair. In these representative embodiments, the implant device comprises the porous β-TCP material of the invention, and optionally at least one bioactive agent.

The implant device comprising the porous β-TCP material serves as a temporary scaffold and substratum for recruitment of migratory progenitor cells, and as a base for their subsequent anchoring and proliferation.

In a representative embodiment, the implant device comprises the porous β-TCP matrix and a bioactive agent, which is dispersed or absorbed in the matrix. It is envisioned that the bioactive agent can include, but is not limited to, bone morphogenic proteins, growth factors such as EGF, PDGF, IGF, FGF, TGF-α and TGF-β, cytokines, MPSF, hormones, peptides, lipids, trophic agents and therapeutic compositions including antibiotics and chemotherapeutic agents, insulin, chemoattractant, chemotactic factors, enzymes, enzyme inhibitors. In representative embodiments, bioactive agents such as vitamins, cytoskeletal agents, autograft, allograft, cartilage fragments, living cells such as chondrocytes, bone marrow cells, mesenchymal stem cells, tissue transplants, immunosuppressants may be added to the porous β-TCP.

In certain embodiments, the porous β-TCP matrix provides a sustained delivery or support system for the bioactive agent, which is released over time at the implantation site as the matrix material is slowly absorbed. In a representative embodiment, the bioactive agent is encapsulated in the biodegradable agent. The resorption of the biodegradable agent and the gradual release of the bioactive agent provides a sustained release system. The dosage and rate of delivery of the bioactive agent may be controlled based on the nature of the porous matrix, the nature of the biodegradable agent and the nature of the binding interaction between the bioactive agent encapsulated in the biodegradable agent, the porous matrix and biodegradable agent.

In yet another representative application, the β-TCP product is part of a prosthetic device. In a representative embodiments, the prosthetic device comprises a surface region that can be implanted adjacent to a target tissue of a mammal, and a composition that is disposed on the surface region. The prosthetic devices will be useful for repairing orthopedic defects, injuries or anomalies in the treated mammal, where in certain embodiments the mammal is a human patient. The prosthetic device may be made from a material comprising metal, ceramic or polymer composite material. Preferred devices comprise a load-bearing core selected from Co—Cr—Mo alloys, titanium alloys and stainless steel. Representative prosthetic devices are selected from the group consisting of a hip device, a fusion cage and a maxillofacial device.

In representative embodiments, the composition comprises the porous β-TCP material of the invention, and optionally, one or more agents selected from the group consisting of a bioactive agent dispersed in the porous β-TCP. The composition may act as a coating for synthetically constructed bone material, such as for an artificial hip, replacement of diseased bone, correction of defects, or anchoring teeth. The composition may be disposed on the surface of the implant in an amount sufficient to promote enhanced tissue growth into the surface. The amount of the composition sufficient to promote enhanced tissue growth may be determined empirically by those of skilled in the art using bioassays, e.g., as described in Rueger et al., U.S. Pat. No. 5,344,654, incorporated herein by reference.

In another representative embodiment, the composition is applied to the clinical procedure of total joint arthroplasty in hips, knees, elbows and other joints, wherein a diseased or damaged natural joint is replaced by a prosthetic joint. For example, in a total hip arthroplasty, an acetabular cup is inserted with the composition in the acetabular socket of the pelvis to replace the natural acetabulum. The cup is held in place by the composition and secured by fixation screws. Generally, the cavity or socket conforms to the outer surface of the acetabular cup. The composition can also be applied to total joint revision surgery, to strengthen the bondage between joint prosthetic devices and the bone.

In yet another representative embodiment, the composition is applied to a clinical procedure called vertebroplasty. The composition is injected into the interior of a vertebral body. This method is used in the treatment of osteoporosis to increase the density of bone.

In a representative embodiment, the prosthetic device is selected from the group consisting of a fusion cage, a dowel and other devices having a pocket or chamber, such as an interbody fusion for containing the composition of the present invention. In certain embodiments, the interbody fusion device is produced from material selected from the group consisting of titanium, PEEK (poly(etheretherketone)) and allograft. The interbody fusion in the cervical, thoracic and lumbar spine can be administered via an anterior or posterior approach. Alternatively, the composition of this invention can be used without an associated interbody device to achieve interbody fusion.

Spinal fusion cages are placed into the intervertebral space left after the removal of a damaged spinal disc to eliminate local motion and to participate in vertebral to vertebra bony fusion. As described in U.S. Pat. No. 5,015,247, incorporated herein by reference, the fusion cages are in the form of a cylindrical hollow member having an outside diameter larger than the space between two adjacent vertebrae to be fused. The interior space within the cylindrical hollow implant can be filled with the composition of this invention. The cylindrical implants can also include a threaded exterior to permit threaded insertion into a tapped bore formed in the adjacent vertebrae. Alternatively, some fusion implants have been designed to be impacted into the intradiscal space. As described in U.S. Pat. No. 6,146,420, incorporated herein by reference, the fusion device includes opposite end pieces with an integral central element. The central element has a much smaller diameter so that the fusion device forms an annular pocket around the central element. The composition of this invention can be disposed within the annular pocket between the opposite end pieces.

In a representative embodiment, the prosthetic device is used for repair of osseous and discoligamentous instability. The composition of this invention may be applied to the intervertebral area, resulting in superior fusion and consequently achieving definitive stabilization of a traumatized motor segment via a single dorsal approach. This application may eliminate the need to undergo a second operation for fractures of the thoracolumbar spine, which, at present, is often necessary but involves additional high risks. Also, this method avoids the problems associated with transplantation of autogenous cancellous bone and its associated risk of high morbidity might be avoided. See, e.g., Rueger et al., Orthopde, 27, pp. 72-79 (1998).

In yet another representative embodiment, the prosthetic device is a maxillofacial device. Maxillofacial devices are applied externally to correct facial defects resulting from cancer surgery, accidents, congenital deformities. In order to restore the masticatory deficiencies, a patient with marginal bone mass is first treated with the composition of this invention to pack and build up the surgical site. A maxillofacial anchoring and distracting system, as illustrated in U.S. Pat. No. 5,899,940, incorporated herein by reference, can be applied to increase the existing bone quality. Fixation devices, such as a standard threaded bone screw and simple pin point tack or self-locking and threaded bone tack screw device (U.S. Pat. No. 5,971,985, incorporated herein by reference), are used for the retention of tissue grafts and synthetic membranes to the maxillofacial bone graft site. Once the site has healed, a second surgery is performed to insert the appropriate length endosseous dental implant and to restore masticatory function.

The invention also provides a method for promoting in vivo integration of an implantable prosthetic device of this invention into a target tissue of a mammal comprising the steps of a) providing on a surface of the prosthetic device a composition comprising the porous β-TCP material, optionally, at least one bioactive agent, and b) implanting the device in a mammal at a locus where the target tissue and the surface of the prosthetic device are maintained at least partially in contact for a time sufficient to permit tissue growth between the target tissue and the device.

The invention also provides a method of inducing bone formation in a mammal, e.g., a human patient. The method comprises the step of implanting in the defect site of a mammal a composition comprising the porous. β-TCP of the invention. In a representative embodiment, the composition may further comprise a bioactive agent. The defect can be an endochondreal defect, an osteochondral defect or a segmental defect. The method can be applied to other defects which include but are not limited to, non-union fractures; bone cavities; tumor resection; fresh fractures (distracted or undistracted); cranial, maxillofacial and facial abnormalities, for example, in facial skeletal reconstruction, specifically, orbital floor reconstruction, augmentation of the alveolar ridge or sinus, periodontal defects and tooth extraction socket; cranioplasty, genioplasty, chin augmentation, palate reconstruction, and other large bony reconstructions; vertebroplasty, interbody fusions in the cervical, thoracic and lumbar spine and posteriolateral fusions in the thoracic and lumbar spine; in osteomyelitis for bone regeneration; appendicular fusion, ankle fusion, total hip, knee and joint fusions or arthroplasty; correcting tendon and/or ligamentous tissue defects such as, for example, the anterior, posterior, lateral and medial ligaments of the knee, the patella and Achilles tendons, and the like as well as those defects resulting from diseases such as cancer, arthritis, including osteoarthritis, and other bone degenerative disorders such as osteochondritis dessicans. The method may be used in bone augmentation, bone prosthesis, hard tissue implant, bone scaffolding, fixation systems (e.g. screws, sutures, suture anchors, staples, surgical tacks, clips, plates and screws).

The invention also provides a method of delivering a bioactive agent at a site requiring bone formation comprising the step of implanting the porous β-TCP and a bioactive agent at the defect site of a mammal. In a representative embodiment, the bioactive agent is encapsulated in a biodegradable agent.

The subject β-TCP products may also find use in calcium phosphate cement compositions. A variety of calcium phosphate cement compositions are known to those of skill in the art, and such cements may be readily modified to include the β-TCP products of the invention. Cement compositions known to those of skill in the art and of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

The following examples are offered by way of illustration and not by way of limitation.

EXPERIMENTAL

I. Porous β-Tricalcium Phosphate (TCP) Production Method

Overview
Porous β-Tricalcium phosphate (β-TCP) is produced by the addition of deliberately sized graphite particulates, followed by evolution of gas by heating to produce porous greenware. Greenware sintering is performed in either: (a) an oxidizing atmosphere; or (b) an inert followed atmosphere followed by an oxidizing atmosphere; to ensure consistent oxidation and removal of the graphite particles near the tricalcium phosphate phase at which solid particles begin to sinter but are still considered solids, thus leaving desired pore structured solid β-TCP.

Methods
To 20 grams reagent grade water was added 20 grams β-TCP powder (Fluka Chemika #21218), 2 grams high purity graphite flakes (Alfa Aesar 10 mesh, #43319), 2 grams graphite powder (Alfa Aesar 200 mesh, #14734), and 1 gram soluble starch (Sigma Chemicals, ACS reagent # S-9765). Compounds were mixed for 5 minutes to form slurry, transferred to a sealed, stainless steel reaction vessel fitted with a pressure relief valve, and heated to approximately 110° C. at approximately 1.5 ATM for 20 minutes or until all water was evaporated. The resulting dried material was then transferred to alumina trays and sintered in air at 1200° C. for eight hours, cooled in air, and ground to produce a product powder of desired particle sizes. Alternatively, sintering may be performed under argon atmosphere, followed by oxygen containing atmosphere (air), ensuring graphite to $CO_2$ conversion nearer to the TCP phase at which solid particles begin to sinter but are still considered solids.

Results
The resulting material was analyzed by several analytical techniques. BET surface area as determined by nitrogen absorption (volumetric technique/micromeritics TriStar 3000) performed by Penn Pharmaceutical Services (United Kingdom) was determined to be 0.273 $m^2g^{-1}$. Porosity as determined by Mercury porosimetry standard intrusion run (Micromeritics 9500 porosimeter) performed by Penn Pharmaceutical Services (United Kingdom) was determined to be 59.5%. X-ray powder diffraction revealed that the material was 97-98% beta tricalcium phosphate. A picture of the material is provided in FIG. 1.

It is evident from the above results and discussion that calcium phosphate cements that set rapidly into compositions with high strength are provided by the subject invention. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of making a porous tricalcium phosphate, said method comprising:
   combining a tricalcium phosphate with graphite to produce a graphite containing tricalcium phosphate composition;
   heating said graphite containing tricalcium phosphate composition to a sintering temperature in an inert atmosphere; and
   sintering said graphite containing tricalcium phosphate composition to produce said porous tricalcium phosphate, wherein said sintering comprises maintaining said composition at said sintering temperature in an oxidizing atmosphere.

2. The method according to claim 1, wherein said tricalcium phosphate is beta-tricalcium phosphate.

3. The method according to claim 1, wherein said graphite containing tricalcium phosphate composition is produced by: combining said tricalcium phosphate and said graphite with water to produce a slurry; and dehydrating said slurry to produce said graphite containing tricalcium phosphate composition.

4. The method according to claim 3, wherein said graphite is made up of graphite compositions of at least two different sizes.

5. The method according to claim 4, wherein said graphite comprises graphite flakes and graphite particles.

6. The method according to claim 3, wherein said dehydrating occurs at a pressure greater than atmospheric pressure.

7. The method according to claim 1, wherein said method further comprises grinding said porous tricalcium phosphate to produce a particulate composition.

8. The method according to claim 1, wherein said sintering occurs at a temperature ranging from about 1100 to about 1300° C.

9. The method according to claim 8, wherein said sintering occurs at a temperature of about 1200° C.

* * * * *

UNITED STATES PATENT AND TRADEMARK OFFICE
CERTIFICATE OF CORRECTION

PATENT NO. : 7,901,650 B2
APPLICATION NO. : 11/165564
DATED : March 8, 2011
INVENTOR(S) : David Delaney Page 1 of 1

It is certified that error appears in the above-identified patent and that said Letters Patent is hereby corrected as shown below:

Title Page, Item 73 Assignee, replace the word "Kinectics" with the word "Kinetics"

Signed and Sealed this
Twenty-ninth Day of May, 2012

David J. Kappos
*Director of the United States Patent and Trademark Office*